United States Patent [19]

Elliott et al.

[11] Patent Number: 5,013,541

[45] Date of Patent: May 7, 1991

[54] POLY(ALPHA-HYDROXY ACRYLIC ACID) AND DERIVATIVES AS ANTITARTAR ACTIVES IN ORAL COMPOSITIONS

[75] Inventors: David L. Elliott, Hawthorne; Catherine L. Howie, Parsippany, both of N.J.

[73] Assignee: Conopco, Inc., New York, N.Y.

[21] Appl. No.: 510,652

[22] Filed: Apr. 18, 1990

[51] Int. Cl.$^5$ .......................... A61K 7/16; A61K 7/18
[52] U.S. Cl. ......................................... 424/52; 424/49
[58] Field of Search ..................................... 424/49, 52

[56] References Cited

U.S. PATENT DOCUMENTS

| | | |
|---|---|---|
| 3,429,963 | 2/1969 | Shedlovsky . |
| 3,934,002 | 1/1976 | Haefele . |
| 4,183,914 | 1/1980 | Gaffar et al. . |
| 4,361,547 | 11/1982 | Sipos et al. . |
| 4,364,927 | 12/1982 | Sipos et al. . |
| 4,627,977 | 12/1986 | Gaffar et al. . |
| 4,661,341 | 4/1987 | Benedict et al. . |
| 4,806,340 | 2/1989 | Gaffar et al. . |
| 4,806,342 | 2/1989 | Gaffar et al. . |
| 4,808,400 | 2/1989 | Gaffar et al. . |
| 4,842,847 | 6/1989 | Amjad . |
| 4,892,724 | 1/1990 | Amjad . |
| 4,892,725 | 1/1990 | Amjad . |

Primary Examiner—Shep K. Rose
Attorney, Agent, or Firm—Milton L. Honig

[57] ABSTRACT

An oral composition is provided which reduces formation of tartar on teeth. The active ingredient is poly($\alpha$-hydroxy acrylic acid) as well as phosphate, sulfate and alkoxy derivatives thereof.

9 Claims, No Drawings

POLY(ALPHA-HYDROXY ACRYLIC ACID) AND DERIVATIVES AS ANTITARTAR ACTIVES IN ORAL COMPOSITIONS

BACKGROUND OF THE INVENTION

1. Field of the Invention

The invention relates to new antitartar agents, dentifrice compositions containing these agents and use of such compositions to control tartar accumulation on teeth.

2. The Related Art

Tartar, known also as calculus, is a hard, mineralized deposit which forms around teeth. This formation arises from deposition of crystals of calcium phosphate in the pellicle and extracellular matrix of dental plaque. Various forms of calcium phosphate have been identified but the most difficult to remove and thermodynamically most stable form is called hydroxyapatite (HAP). Amorphous forms of calcium phosphate are believed to be the precursors of HAP. Regular brushing can usually remove the amorphous forms but is not fully effective to dislodge the final stable calculus form. Therefore it is desirable to prevent amorphous forms of calcium phosphate from transforming into HAP. The art has recognized that agents which interfere with the formation of HAP crystallization will be effective antitartar agents.

Polymers, especially those of the anionic type, have been found to be effective antitartar agents. U.S. Pat No. 4,661,341 (Benedict et al) discloses polyacrylic acids of molecular weight 3500 to 7500 for use in oral antitartar compositions. Comonomers specified include hydroxyalkyl acrylates or methacrylates and acrylamides. U.S. Pat. No. 3,429,963 (Shedlovsky) teaches use of maleate-containing copolymers and vinyl sulfonates in oral compositions. Typically, low molecular weight anionic materials of high charge density are preferred in the known art. For example, U.S. Pat. No. 4,183,914 (Gaffar et al) discloses use of polymaleates as antitartar agents; however, these materials cannot be obtained above molecular weight 1000, and often have low purity in commercial samples. These polymeric materials have poor appearance, taste, and safety as a consequence of high impurity levels deriving from the manufacturing process.

Polymers have also been found to give benefits other than crystal-growth or transformation inhibition. Gaffar et al. in a series of patents reports use of synthetic linear anionic polymers of higher molecular weight for use in combination with inorganic pyrophosphates in oral compositions. See U.S. Pat. No. 4,627,977; U.S. Pat. No. 4,806,340; U.S. Pat. No. 4,806,342; U.S. Pat. No. 4,808,400 and U.S. Pat. No. 4,808,401. These polymers were found to inhibit the action of pyrophosphatase in the mouth thereby allowing greater efficacy of the pyrophosphate. Preferred were the methyl vinyl ether/maleic anhydride copolymers sold by GAF Corporation under the Gantrez trademark. These materials have molecular weights which are between 50-500,000, although a broader range (1000 to 1 million) is specified in the patents.

Other polymers have been found to inhibit the growth or adhesion of microbials, resulting in reductions of plaque and therefore degree of tartar buildup. Sipos et al. in U.S. Pat. No. 4,364,927 and U.S. Pat. No. 4,361,547 discloses several types of sulfonated aromatic polymers which are effective in reducing plaque formation.

Thus, most of the prior art teaches polymeric materials which are either good crystal growth inhibitors or good antiplaque agents. It would be beneficial to have polymeric agents which were effective in both functions, i.e., effectively inhibit transformation of brushite to hydroxyapatite, and in addition reduce plaque buildup on oral surfaces.

Accordingly it is an object of the present invention to provide an antitartar agent functioning both to inhibit transformation of brushite to hydroxyapatite and also to reduce plaque buildup on oral surfaces.

A further object of the present invention is to provide new oral compositions and a method for more effectively controlling buildup of plaque and tartar on teeth.

These and other objects of the present invention will become more readily apparent in view of the detailed description and Examples which follow.

SUMMARY OF THE INVENTION

An oral composition is provided comprising:

(i) An effective amount to prevent tartar formation of a polymer whose structure is:

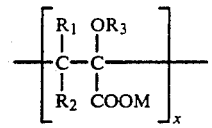

wherein:

$R_1$ and $R_2$ may independently be selected from the group consisting of hydrogen and $C_1$-$C_3$ alkyl;

$R_3$ is selected from the group consisting of hydrogen, phosphate, sulphate and $C_1$-$C_{22}$ alkyl;

M is selected from the group consisting of hydrogen, alkali metal, alkaline earth metal, ammonium, alkanolammonium, transition metal cations and mixtures thereof;

x is an integer from 3 to 10,000; and (ii) an effective amount of a carrier to convey the polymer into an oral cavity.

A method is also herewith provided for inhibiting tartar formation in the mouth by applying to the teeth an oral composition containing the aforementioned polymer in a suitable carrier. Particularly preferred as the polymer is poly(α-hydroxy acrylic acid).

DETAILED DESCRIPTION OF THE INVENTION

Now it has been found that poly(α-hydroxy acrylic acid), hereinafter identified as PHAA, as well as its phosphate, sulfate and $C_1$-$C_{22}$ alkoxy derivatives, are effective antitartar agents. These materials were found to have better performance, as shown in vivo tests, than polyacrylates and polymaleates of the known art. Polymers of this invention were also identified through in vitro tests as being brushite transformation inhibitors with activity comparable to that of the known polyacrylates.

Antitartar polymers of this invention will have the following structure:

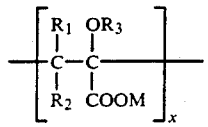

wherein:

$R_1$ and $R_2$ represent hydrogen or a $C_1$–$C_3$ alkyl group;

$R_3$ represents either hydrogen, phosphate, sulfate or a $C_1$–$C_{22}$ alkyl group.

M represents hydrogen, alkali metal, alkaline earth metal, ammonium alkanolammonium, transition metal cations and mixtures thereof; and x is an integer from 3 to 10,000.

Particularly preferred cations M are those of copper and zinc. Amounts of polymer to transition metal cation may range in weight from about 20:1 to 1:1, preferably about 10:1 to about 5.1.

Copolymers containing combinations of monomer units with varying $R_1$, $R_2$ and $R_3$ groups may also be effective. Advantageously, when the copolymers include a phosphate, sulfate or $C_1$–$C_{22}$ alkyl substituted monomer unit at least 25% of the remaining monomer units should be α-hydroxy acrylic acid or salt units. All forms of the polymer of this invention should be water-soluble or at least partially water-soluble. Homopolymers of α-hydroxy acrylic acid are preferred, as well as polymers of PHAA where 1–75% of the hydroxyl groups are substituted with either phosphate or sulfate groups.

Copolymers containing monomer units of the aforedescribed structure at levels of at least 3 mole % may also be employed, provided that the second comonomer does not deleteriously affect the solubility of the resultant polymer. Copolymers of hydroxy acrylic acid with acrylic acid, methacrylic acid, maleic acid, acrylamido monomers, or hydroxyalkyl acrylates or methacrylates are preferred.

Molecular weights of the polymers according to this invention should range from about 400 to 2 million, preferably from about 1,000 to 100,000, optimally between about 5000 to about 60,000.

Amounts of the polymer of this invention should be present in the oral composition from about 0.1 to about 10% by weight, preferably from about 0.4 to about 7%, optimally between about 1 to about 5%. The final oral composition should not contain any components or level of components which deleteriously affect the anti-tartar activity of the polymers of the invention.

Carriers suitable for use with the polymers are preferably hydroxylic materials such as water, polyols and mixtures thereof. Polyols, sometimes referred to as humectants, include glycerol, sorbitol, propylene glycol, lactitol, xylitol, polypropylene glycol, polyethylene glycol, hydrogenated corn syrup and mixtures thereof. Particularly preferred as the carrier is a liquid mixture of 3–30% water, 0–80% glycerol and 20–80% sorbitol. Generally the amount of carrier will range from about 25 to 99.9% by weight, preferably from about 70 to 95% by weight.

When the oral compositions are in the form of a toothpaste or gel there will typically be included a natural or synthetic thickening agent in an amount from 0.1–10%, preferably about 0.5–5% by weight. Thickeners may include alkyl cellulose, hydroxy cellulose, xanthan gum, tragacanth gum, karaya gum, arabic gum, Irish moss, starch, alginates and carrageenans. The amount of thickening agent will generally be between about 0.1 and 10% by weight.

Surfactants are normally also included in the oral compositions of this invention. These surfactants may be of the anionic, nonionic, cationic or amphoteric type. Most preferred are sodium lauryl sulfate, sodium dodecylbenzene sulfonate and sodium laurylsarcosinate. Surfactants are usually present in an amount from about 0.5 to 5% by weight.

When in the form of a toothpaste or gel, the oral compositions will normally include an abrasive. Abrasives may be selected from water-insoluble alkali or alkaline earth metal salts of metaphosphate, calcium carbonate, aluminates and silicates. Especially preferred are silicate, dicalcium phosphate and calcium carbonate. Amounts of the abrasive will range from about 5% to about 80% by weight.

Adjunct tartar control agents, especially those containing phosphorous, may be combined with the polymers of the present invention. Inorganic phosphorous adjuncts may include any of the water-soluble pyrophosphates such as disodium pyrophosphate, dipotassium pyrophosphate and mixtures of these with tetrapotassium pyrophosphates or tetrasodium pyrophosphates. Organic phosphorous compounds that may serve as adjuncts include polyphosphonates such as disodium ethane-1-hydroxy-1, 1-diphosphonate(EHDP) and methanediphosphonic acid, and 2-phosphonobutane-1,2,4.-tricarboxylic acid.

For anti-caries protection, a source of fluoride ion will normally be present in the oral compositions. Fluoride sources include sodium fluoride, potassium fluoride, calcium fluoride, stannous fluoride, stannous monofluorophosphate and sodium monofluorophosphate. These sources should release anywhere from 25 to 3500 ppm of fluoride ion. The anti-caries agent will be present in an amount from about 0.05 to about 3% by weight, preferably 0.5 to 1% by weight.

Flavors that are usually present in the oral compositions are those based on oils of spearmint and peppermint. Examples of other flavoring materials include menthol, clove, wintergreen, eucalyptus and aniseed. Flavors may range in concentration from 0.1 to 5% by weight.

Sweetening agents such as saccharin, sodium cyclamate, aspartame, sucrose and the like may be included at levels from about 0.1 to 5% by weight.

Other additives may also be incorporated into the oral compositions including preservatives, silicones, other natural or synthetic polymers, and anti-gingivitis actives.

The following examples will more fully illustrate the embodiments of this invention. All parts, percentages and proportions referred to herein and in the appended claims are by weight of the total composition unless otherwise stated.

EXAMPLE 1

Sandoperol PLA (MW 5000) and Sandoperol PL (MW 60,000), products of Sandoz Chemicals, were used as commercially-available forms of PHAA. To prepare these materials for use, powder samples of the desired amount were weighed and dispersed in water, and the pH adjusted to about 8. Upon neutralization of the polymer to the alkali salt form, the polymer becomes fully-dissolved thereby forming a homogeneous solution. Table I lists information about other commercial carboxylate polymers mentioned for comparative purposes in the other examples.

TABLE I

| Sample | Supplier | Composition | Molecular Weight |
|---|---|---|---|
| Sokalan CP5 | BASF | 4:1 Acrylic acid/ Maleic acid | 70,000 |
| PA25PN | BASF | Polyacrylic acid | 4,000 |
| DKW-125 | National Starch | " | 6,000 |
| Belclene 201 | Ciba-Geigy | Polymaleic acid | 1,000 |
| Gantrez S-97 | GAF | 1:1 Maleic anhydride/ methyl vinyl ether | 70,000 |

EXAMPLE 2

Rat Calculus Assay

The polymers of this invention were tested in vivo using a rat calculus assay. In this test, litters from Sprague-Dawley pregnant female rats (ex Charles River) were weaned (21 days old), weighed, tagged and split into cells of 25 animals balanced by gender and litter. Subjects were housed in pairs and were fed a calculogenic diet (consisting of 50% cornstarch, 32% nonfat powdered milk, 5% cellulose flour, 5% sucrose, 3% liver powder, 1% cottonseed oil, 2.7% sodium phosphate, 1% calcium chloride dihydrate, and 0.3% magnesium sulfate) with filtered city water. Subjects were treated with test solutions twice a day for three weeks. At the end of the test period, the teeth were scored in a blind protocol using a modified Frances & Briner method (*J. Dental Res.* 48(6) p. 1185-94 1969). A Nikon Stereoscopic Microscope was used for the evaluation (20× magnification).

The samples were prepared as rinse formulations containing 5% concentration of the agent. One hundred and fifty microliters (150 μL) of rinse was delivered to each subject using a 1 cc syringe. Deionized water with no agent added was used as the control sample.

The results of the tests are shown in Table II for several polymers along with their trade names and previous references which disclose their use as antitartar agents. The term % inhibition is used as a measure of the reduction in tartar or calculus found on the teeth relative to the control sample.

TABLE II

| Results from the In Vivo Rat Calculus Trial | | | |
|---|---|---|---|
| Polymer | Trade Name | % Reduction | Reference |
| Maleic acid/methyl vinyl ether | Gantrez S-97 | 2% | U.S. 4,627,97 |
| Polyacrylate, MW = 6000 | DKW-125 | 6% | U.S. 4,661,34 |
| Acrylate/maleate copolymer | Sokalan CP5 | 10% | EP 321,65 |
| Polymaleate | Belclene 201 | 21% | U.S. 4,183,91 |
| PHAA, MW = 5000 | Sandoperol PLA | 22% | — |

The results indicate that significant reduction in calculus is found for the PHAA material. In addition, this material gives higher scores than the comparative polymers, including a polyacrylate of comparable molecular weight. The comparative examples are known from previous art to have antitartar activity.

EXAMPLE 3

Microbial Mineralization

PHAA and several other polymeric materials were assessed using an in vitro microbial mineralization assay. Standard glass stirring rods were placed in an aqueous solution containing *Streptococcus mutans,* one of the microbes found in the human oral cavity. Microbes were allowed to grow onto the rods for about 2 days. The rods were then removed from the solution and placed in a treatment solution containing antitartar agents at levels of about 1.25 wt %. Treatment with a solution containing only deionized water was used as a control. After treatment for about 30 seconds, the rods were placed in a calcifying medium made up of calcium and phosphate at levels of 1.5 mM and 5.0 mM, respectively. The calcifying medium was supplemented with about 25% human saliva. The glass rods were mineralized in the calcifying medium for 4 days. Thereafter, the level of tartar formation was assessed via calcium and phosphorus analysis. Results were calculated by comparing the % reduction of tartar formation to that of the control. Table III lists results of the experiments.

TABLE III

| Results from In Vitro Microbial Assay* | |
|---|---|
| Treatment | % Reduction |
| Gantrez S-97 | 4 |
| Sokalan CP5 | 10 |
| Polyacrylate (PA25PN) | 45 |
| PHAA (Sandoperol PLA) | 40 |

*All agents tested at 1.25% level

The results in Table III indicate that PHAA is about equal in effectiveness to polyacrylate in reducing microbial growth and subsequent calcification. PHAA was however more effective than Gantrez and Sokalan, thereby correlating with the in vivo assay (Example 2).

EXAMPLE 4

Brushite Transformation Assay

Brushite (20 mg) of surface area 3 m²/g from Albright & Wilson which was free of stabilizers was suspended in 5 ml of 0.25 M imidazole buffer at pH 7.4 and incubated at 33° C. Agents were added to the buffer solution at desired levels and tested for their ability to inhibit the transformation of brushite to hydroxyapatite. Hydrolysis of the brushite (transformation) was followed by measuring the increase in supernatant phosphate in the buffer solution at 6 and 24 hours. The phosphate level was determined using the method of Chen et al. (*Anal. Chem.* 8, 1756 (1956)). Untreated brushite was used as the control. Table IV lists results from tests using a series of polymeric agents.

TABLE IV

| Results From the In Vitro Transformation Assay | |
|---|---|
| Agent | Threshold Concentration* |
| Belclene 201 | 3 ppm |
| PA25PN | 3 ppm |
| Gantrez S-97 | 10 ppm |
| Sandoperol PLA | 3 ppm |

*Threshold Concentration is defined as the minimum level of agent required to give 100% inhibition of brushite transformation to HAP at 33° C. for 24 hours.

As shown in Table IV, PHAA (Sandoperol PLA) performed equally as effective as polyacrylate (PA25PN) or polymaleate (Belclene) in this in vitro assay. Gantrez was not as effective. Thus, the inhibitory activity of PHAA in this assay was equal to that of typical antitartar agents disclosed in the art.

EXAMPLE 5

Seeded Crystal Growth Inhibition Assay Combinations with Zinc

Zinc salts of the polymers of this invention were tested in vitro using a Seeded Crystal Growth Inhibition Assay. This assay involved the treatment of synthetic hydroxyapatite (HAP) with a potential antitartar agent. The treated HAP was incubated at 37° C. in a calcifying solution made up of calcium and phosphate at 1.5 mM and 4.5 mM, respectively. The samples were filtered to remove any calcium phosphate crystals and the free calcium in the filtrate was measured using Atomic Absorption Spectroscopy. The inhibition was calculated as follows:

Inhibition = [Ca] depletion from control−[Ca] depletion from sample
[Ca] depletion from control The % inhibition is a measure of the degree of inhibition of calcium phosphate precipitation.

Table V below lists results of seeded crystal growth inhibition experiments. The term "synergy" is used to demonstrate the enhanced effect of the polymer/zinc combination over the two individual components. For example, in the 1%/0.2% pairing the expected result from the combination would be (8%+45%)=53% inhibition; the actual value was 82%, resulting in a synergy of (82%−53%)= +29.

TABLE V

| Poly-hydroxyacrylic acid in water (wt. %) | Zn(acetate)$_2$ (wt. %) | % Inhibition | Synergy |
|---|---|---|---|
| 1% Sandoperol PLA | — | 8% | — |
| — | 0.2% | 45% | — |
| 1% Sandoperol PLA | 0.2% | 82% | +29 |
| 1% Sandoperol PL | — | 9% | — |
| — | 0.06% | 40% | — |
| 1% Sandoperol PL | 0.06% | 76% | +27 |

The results in Table V indicate that synergistic increases in inhibition occur for combinations of the polymers with zinc salts.

EXAMPLE 6

The following Example illustrates a high abrasive containing toothpaste of the present invention.

| Ingredient | % Weight |
|---|---|
| Dicalcium phosphate dihydrate | 40.0 |
| Sodium pyrophosphate | 5.0 |
| Sodium carboxymethylcellulose | 1.0 |
| Glycerol | 20.0 |
| Sorbitol | 10.0 |
| Sandoperol PLA | 1.6 |
| Sodium lauryl sulfate | 1.5 |
| Water | 20.9 |

EXAMPLE 7

The following Example illustrates a typical gel dentifrice of the present invention.

| Ingredient | % Weight |
|---|---|
| Silica polishing agent[1] | 15.00 |
| Silica polishing agent[2] | 8.00 |
| Sodium carboxymethylcellulose | 0.84 |
| Sorbitol | 36.00 |
| Saccharin | 0.20 |
| Sandoperol PLA | 1.25 |
| Flavor | 1.30 |
| TiO$_2$ | 0.50 |
| Colorant (1% soln.) | 0.02 |
| Sodium Hydroxide | 0.10 |
| Sodium lauryl sulfate-glycerine[3] | 7.00 |
| Water | Balance to 100% |

[1]Syloid 63 is a silica aerogel having an average particle character of 4–10 microns
[2]Syloid 244 is a silica aerogel having an average particle diameter of 3 microns.
[3]A solution of 21 parts sodium lauryl sulfate in 79 parts glycerol.

EXAMPLE 8

The following Example illustrates a typical mouthwash composition according to the present invention.

| Ingredient | % Weight |
|---|---|
| Glycerol | 35.00 |
| Ethanol | 27.00 |
| Polyethylene glycol | 10.00 |
| Flavor, color | 0.90 |
| Sandoperol PLA | 0.45 |
| Polyoxyethylene sorbitan monolaurate | 0.20 |
| Water | Balance to 100% |

EXAMPLE 9

The following Example illustrates a standard toothpaste composition according to the present invention.

| Ingredient | % Weight |
|---|---|
| Alumina trihydrate | 50.00 |
| Sorbitol syrup (70% solution) | 27.00 |
| Sodium lauryl sulfate | 1.50 |
| Sandoperol PLA | 1.50 |
| Sodium carboxymethyl cellulose | 0.85 |
| Sodium monofluorophosphate | 0.76 |
| Sodium saccharin | 0.20 |
| Titanium dioxide | 0.50 |
| Flavor | 1.00 |
| Water (demineralized) | Balance to 100% |

The foregoing description and Examples illustrate selected embodiments of the present invention and in light thereof various modifications will be suggested to one skilled in the art, all of which are in the spirit and purview of this invention.

What is claimed is:

1. An oral dentifrice, toothpaste or rinse composition whose essential antiplaque and antitartar agent consists of:

(i) an effective amount to prevent tartar formation a polymer whose structure is:

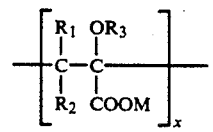

wherein:
   $R_1$ and $R_2$ may independently be selected from the group consisting of hydrogen and $C_1$-$C_3$ alkyl;

$R_3$ is selected from the group consisting of hydrogen, phosphate, sulphate and $C_1$-$C_{22}$ alkyl;

M is selected from the group consisting of zinc and copper;

x is an integer from 3 to 10,000; and (ii) an effective amount of a carrier to convey the polymer into an oral cavity.

2. A composition according to claim 1 wherein said carrier is selected from the group consisting of water, polyols and mixtures thereof.

3. A composition according to claim 2 wherein said polyol is selected from the group consisting of glycerol, sorbitol, propylene glycol, lactitol, xylitol, polypropylene glycol, polyethylene glycol, hydrogenated corn syrup and mixtures thereof.

4. A composition according to claim 1 further comprising a source of fluoride ion present in an amount from about 25 to 3500 ppm.

5. A composition according to claim 1 wherein the polymer is poly(α-hydroxy acrylic acid) in zinc salt form.

6. A composition according to claim 1 wherein said polymer has a molecular weight ranging from about 5000 to about 60,000.

7. A composition according to claim 1 wherein said polymer is present in an amount from about 0.1 to about 10% by weight.

8. A composition according to claim 1 where said polymer is formed from at least two different acrylic type monomers.

9. In a method to inhibit formation of tartar on teeth comprising applying into an oral cavity a composition comprising:

(i) an effective amount to prevent tartar formation of a polymer whose structure is:

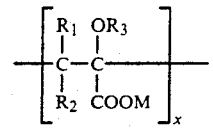

wherein:

$R_1$ and $R_2$ may independently be selected from the group consisting of hydrogen and $C_1$-$C_3$ alkyl;

$R_3$ is selected from the group consisting of hydrogen, phosphate, sulphate and $C_1$-$C_{22}$ alkyl;

M is selected from the group consisting of hydrogen, alkali metal, alkaline earth metal, ammonium, alkanolammonium, transition metal cations and mixtures thereof;

x is an integer from 3 to 10,00; the improvement wherein a synergistic inhibition of tartar formation is obtained by the step of including an effective amount of a zinc or copper salt in an effective amount of a carrier to convey the polymer into an oral cavity.

* * * * *